United States Patent
Furtwängler

(10) Patent No.: US 6,794,612 B2
(45) Date of Patent: Sep. 21, 2004

(54) MODELING DEVICE

(76) Inventor: Bernhard Furtwängler, Leberstrasse 56, D-10829 Berlin (DE)

( * ) Notice: Subject to any disclaimer, the term of this patent is extended or adjusted under 35 U.S.C. 154(b) by 0 days.

(21) Appl. No.: 10/275,165

(22) PCT Filed: Mar. 27, 2001

(86) PCT No.: PCT/EP01/03459

§ 371 (c)(1),
(2), (4) Date: Nov. 1, 2002

(87) PCT Pub. No.: WO01/82823

PCT Pub. Date: Nov. 8, 2001

(65) Prior Publication Data

US 2003/0089695 A1 May 15, 2003

(30) Foreign Application Priority Data

Apr. 5, 2000 (DE) .......................... 200 07 821

(51) Int. Cl.[7] .................. H05B 3/02; A46B 11/08; B05C 17/005
(52) U.S. Cl. .................. 219/227; 401/2; 222/146.5
(58) Field of Search .................. 219/227, 237; 433/32; 401/1–3, 150; 222/146.5, 630, 575

(56) References Cited

U.S. PATENT DOCUMENTS

| | | | | |
|---|---|---|---|---|
| 4,553,935 A | * | 11/1985 | Ueno | 433/32 |
| 4,582,488 A | | 4/1986 | Newman | 433/81 |
| 4,639,155 A | * | 1/1987 | Schuster et al. | 401/1 |
| 4,953,755 A | * | 9/1990 | Dennison | 222/146.5 |
| 6,255,625 B1 | * | 7/2001 | Baschenis | 219/227 |

FOREIGN PATENT DOCUMENTS

| | | | | |
|---|---|---|---|---|
| DE | 33 46 254 A1 | | 7/1985 | B05C/9/14 |
| DE | 89 07 773.3 | | 9/1989 | A61C/9/00 |
| DE | 4241092 | * | 6/1994 | |
| DE | 94 12 336.5 | | 12/1994 | A61C/13/34 |
| EP | 356588 | * | 3/1990 | |
| EP | 423388 | * | 4/1991 | |
| FR | 2556984 | * | 6/1985 | |
| FR | 2 602 669 | | 7/1986 | A61C/5/04 |

OTHER PUBLICATIONS

Dental–Labor, XLVII, Heft Apr. 2000, p. 554.

* cited by examiner

*Primary Examiner*—John A Jeffery
(74) *Attorney, Agent, or Firm*—Synnestvedt & Lechner LLP

(57) ABSTRACT

A modeling device intended for applying wax to the crown region of a tooth which is to be modeled is designed for the purpose of improving its characteristics in use such as its handling during modeling work, when inserting new wax cartridges etc. as an elongated, writing device-like base body, which includes at one end a modeling tip and inside accommodates a forward feed drive for a wax cartridge and a heating device which is used to render the wax to be processed into a liquid state at the end facing the modeling tip, so that as the forward feed drive is actuated liquid wax can be discharged from the outlet. For the purpose of supplying electric energy a cable is attached to the front side end and in fact to the concave side of the curved modeling tip.

50 Claims, 7 Drawing Sheets

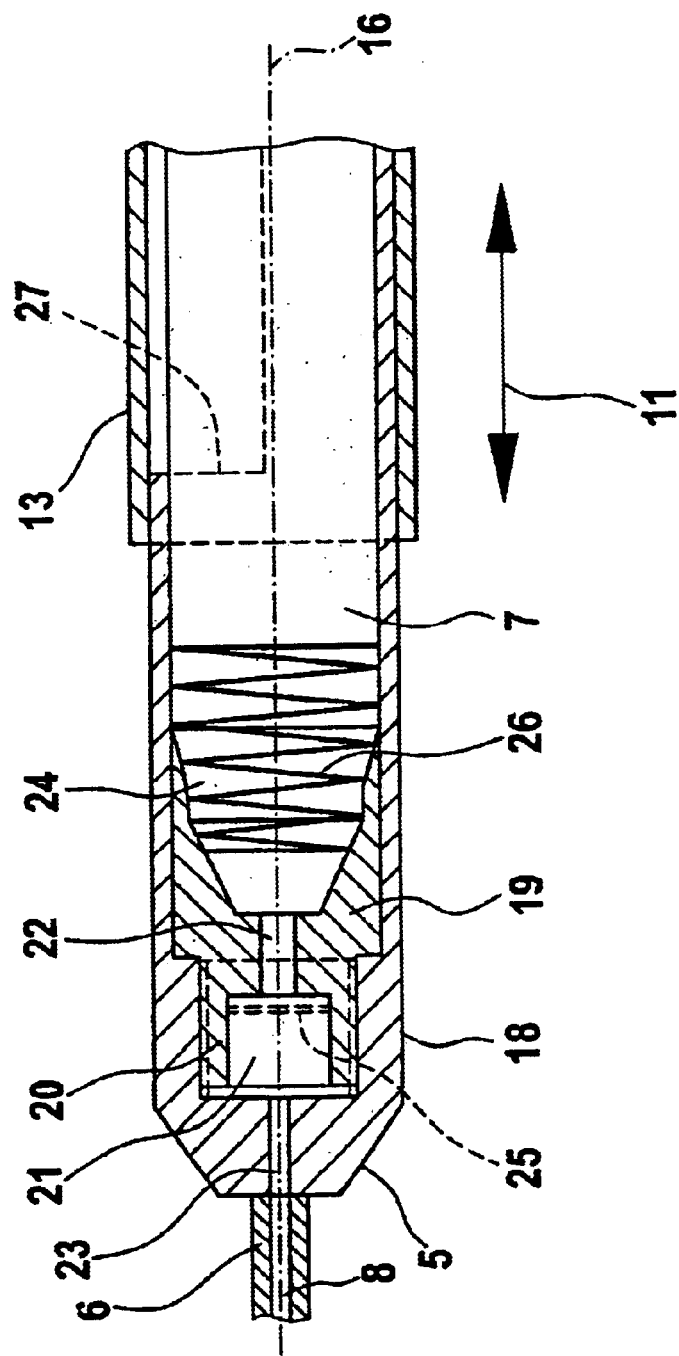

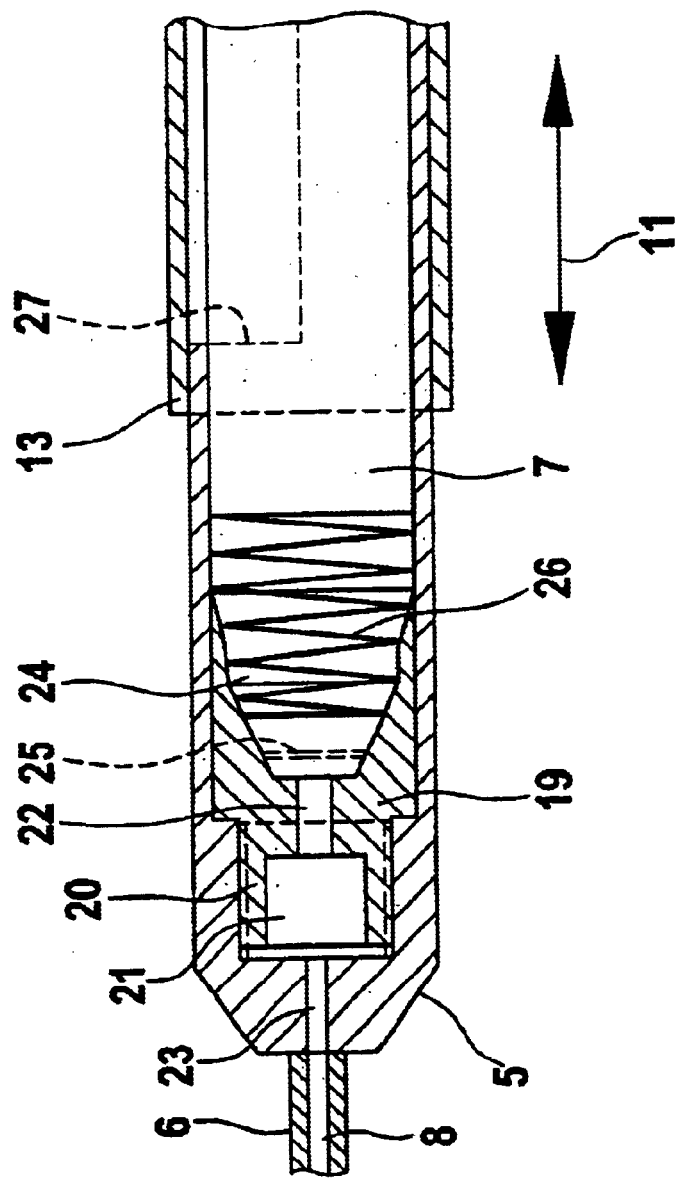

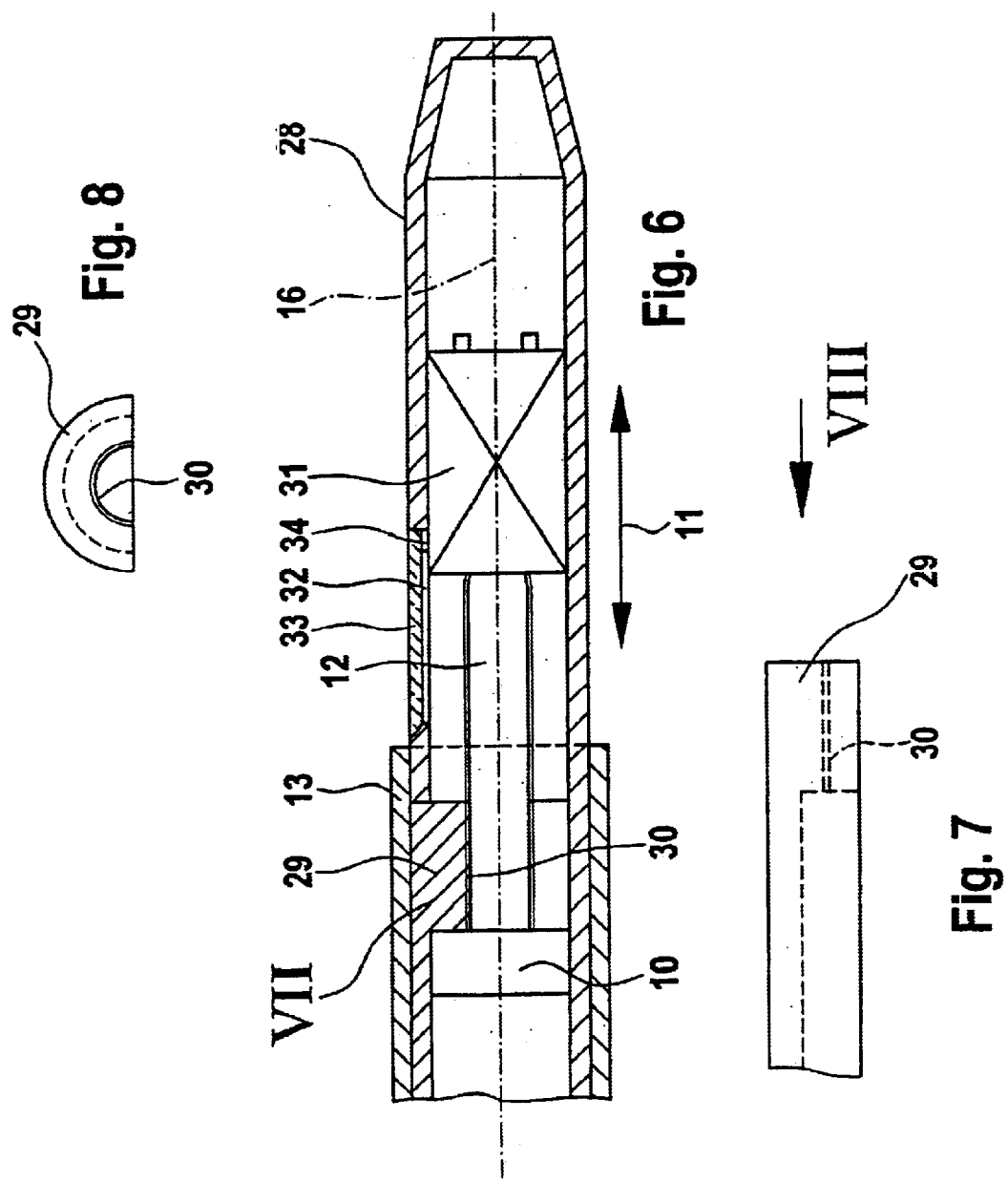

MODELING DEVICE

FIELD OF THE INVENTION

The invention relates to a modeling device for manually applying and modeling substances, namely wax, which are flowable when subjected to heat.

BACKGROUND OF THE INVENTION

Modeling devices are known per se in connection with various functions, in particular for various materials. One important application area relates to prosthodontics, in particular the application of wax to the crown region of a tooth to be modeled. It is known on the one hand such that by means of a modeling tip wax is received in a flowable consistency, i.e. it can be modeled in a plastic manner, and transferred to the crown region, where it is subsequently worked. As the spatial structures to be worked are relatively small, this activity requires that the wax to be applied is metered in an extremely precise manner. Also, it is laborious and time-consuming using a modeling tip for the flowable wax to be received and applied at a site which is remote from the processing location.

A modeling device is known from Dental-Labor XLVIII, Issue 4/2000, wherein a tank which receives a wax cartridge is provided within a modeling device and said tank can be heated electrically to the same extent as a modeling tip. A mechanical push button is used to meter the wax which issues out of the modeling tip and the modeling device is operatively connected to an energy supply unit.

A device for wax modeling cast models in dentistry is known from German Patent DE 94 12 336 U1, which device consists of an elongated, base body which is a similar shape to a writing device and which serves as a storage chamber for the wax and whose funnel-shaped end region is provided with an outlet orifice and a coupling part, onto which coupling part conventional modeling tips can be placed. The wax storage chamber is encompassed by electrically heatable heating elements in the form of a heating mat which is connected to a thermostat, adjusting elements and a display device. Once the entire wax storage chamber has been heated, a heat insulation layer is provided between the casing of the base body and the heating mat. The end region, remote from the modeling tip, of the base body serves to insert wax cartridges known per se into the wax storage chamber, wherein likewise a pneumatically operated piston-cylinder unit is inserted via this end region into the base body and forms a forward-feed drive. For control purposes, the device is provided with sensor buttons which are located on the front side end of the base body facing the modeling tip. Depending upon the temperature of the melted wax inside the wax storage chamber, it can be difficult to meter in a precise manner the wax to be dispersed. It is a drawback as far as the operating technology is concerned, that the end remote from the modeling tip is not only connected to lines for supplying compressed air but is also connected to lines for supply electrical energy. This not only impairs the view of the immediate working region of the modeling tip but precise movements are also difficult. A further unfavorable condition is the complete encasement of the wax storage chamber in a heat-insulating material, as this inevitably leads to an increase in the cross-sectional dimensions of the device.

A further comparable device is known from German Patent DE 33 46 254 A1, which device consists of an elongated base body, wherein the wax cartridges to be processed can be inserted either via the rear side end of the base body or via the front side end thereof, in other words, in each case having first dismantled the function elements located on these two ends. However, as a departure from the subject matter of the aforementioned DE 94 12 336 U1, only the frontal side end is heated, i.e. the end facing the modeling tip, so that there is no necessity to encase the wax storage chamber in a heat-insulating casing. The forward-feed drive used can comprise an electromotor or also a piston cylinder unit requiring a supply of compressed air. However, a disadvantage of this known device is also the condition that connection lines for supplying electrical energy and optionally also for supplying the compressed air are located on the rearside end, i.e. the end remote from the modeling tip. Finally, it is comparatively complicated to use a wax cartridge which is to be processed.

SUMMARY OF THE INVENTION

It follows from this that the object of the invention is to provide a modeling device in accordance with the generic type such that in addition to facilitating the handling of the modeling device, the metering of the substance to be applied and the application procedure as such are also facilitated. This object is achieved in the case of such a device by virtue of a stylus having a chamber and a closable opening therein for inserting a wax cartridge into the chamber, a piston being positioned within the chamber and connected to a spindle nut and a threaded spindle, the piston forming the force-transmitting member between the threaded spindle and the modeling substance, a cable from an energy supply being attached to a front region of the stylus facing a modeling tip positioned on the front region.

In a manner known per se, a motorized forward-feed drive for the substance to be processed is located inside the modeling device and the intended purpose of the said drive is to move this substance for processing in the direction towards the modeling tip. Morever, a heating device is provided, which is capable of heating the substance substantially only at the end of the device facing the modeling tip and in particular until it issues out of the outlet of the modeling tip. In other words, it is not the intention to heat the substance completely to render it all into a liquid state, which in addition to other disadvantages would not only be associated with a certain expenditure of time but would simultaneously also be associated with a corresponding expenditure of energy. Thus, only that region of the substance is heated which during the procedure of being applied to the crown region to be modeled, namely when exiting out of the said outlet, is subjected to plastic deformation and accordingly must be sufficiently flowable. Finally, a switching device is provided, which is connected directly to the modeling device and during the working procedure is subjected to the immediate influence of the user of the modeling device. This switching device serves to control both the forward feed drive and also the heating device. It is preferably provided that the forward feed rate can be continuously regulated within a fixed feed rate range which is tailored to suit the working process. The same applies for the heating device. In particular, the heat which is to be imparted into the substance being processed can preferably be regulated likewise within a fixed range. The user of the modeling device thus has the opportunity to control both the forward feed and also the consistency of the substance being processed in a manner tailored to suit the working step and also the characteristics of the substance.

In accordance with the invention, the base body of the modeling device or stylus is provided with an orifice which is intended for introducing the substance which is a solid body in its initial state. This orifice can be closed and any flap or closing mechanism which does not impair the handling of the modeling device may be used for this purpose.

The components of the forward feed drive in accordance with the invention are formed by an electromotor, a threaded spindle and a spindle nut, wherein for example the threaded spindle is mounted in a non-rotatable manner within the modeling device, so that a rotation of the spindle nut can generate a forward feed movement in the longitudinal direction of the modeling device. The rotational speed of the motor and the pitch of the threaded spindle are designed with respect to the control range of the forward feed rate. A piston which is connected to the threaded spindle serves to provide a large-surface force-transmitting element which is directly connected to the substance which is to be processed. Both for reasons of weight and also to avoid the view being impaired, the cable is preferably attached to the front side end of the modeling device, i.e. the end of the modeling device facing the modeling tip, and extends—in the direction towards the front side—at an acute angle with respect to the longitudinal axis of the modeling device. This embodiment also serves to simplify the practical handling and thus ensures a working result of high quality.

The heating device can be formed by a coil arrangement which serves to heat that part of the substance being processed which is facing the front side region, i.e. the region adjacent to the modeling tip. In a particularly advantageous manner it is possible to provide several coils which are independent of each other and whose heating capacities can be controlled independently of each other. In this manner one coil can serve to provide basic heating and a further coil is designed merely for providing power peaks. The coils can be controlled, as far as their heating capacity is concerned, independently of each other. However, it is also possible to use in place of the coil arrangements any other flat surface heat conductor structures which heat up as a result of a current passing through them and which are designed to transmit heat to the substance which is being processed.

The molding tip comprises an end section which is bent at an angle with respect to the longitudinal axis of the modeling device. An alternative arrangement could also be a corresponding curvature. This embodiment improves the line of view of the respective user to the site where the substance is currently being applied. The same applies for the site where a modeling procedure is being performed using the modeling tip. This embodiment thus improves the working opportunities in the chewing surface depth.

The switching elements of said device are formed by sensors which render it possible to perform switching procedures without jarring so that neither the application procedure nor the metering and modeling procedure are impaired by these switching procedures. The extent to which the heating and to the same extent the forward feed movement can be controlled is selected in dependence upon the characteristics of the substance which is to be processed.

The modeling or dispensing tip of the modeling device can in addition be heated in a controlled manner. In this way, the forward feed and the procedure of metering the substance which is to be processed can be further improved.

The modeling device can be provided with an end switch which then triggers the automatic return of the forward feed drive to its initial position when the substance which is to be processed has been dispensed from the modeling device.

In the forward feed drive, a spindle nut is fixed, i.e. it is disposed within the elongated base body or stylus of the modeling device in such a manner as not to displace axially or rotate and a threaded spindle is provided which at one end is connected to the piston which is intended for forward feeding the wax cartridge which is to be processed and at its opposite end is connected to the motor. Both the piston and also the motor are arranged within the stylus in a non-rotatable manner, so that a rotational movement on the threaded spindle creates a corresponding axial displacement of the entire assembly consisting of the threaded spindle, motor and piston. The spindle nut fixedly arranged within the casing is located on the end of the stylus remote from the modeling tip, in particular the said cut-out.

The spindle nut can be designed fundamentally merely in the shape of a half-shell, so that a threaded engagement with the thread of the spindle shaft is only over a periphery of 180°. It has been established that such a limited threaded engagement can be regarded fundamentally as sufficient for the purposes of the subject of the invention. Furthermore, the spindle nut can also be formed as a longitudinally-divided body which consists of two half-shells which in their entirety can be completed to form a full cylindrical shell. Both variants offer fundamentally simple opportunities of releasing the threaded engagement between the spindle nut and the threaded spindle so that in the released state the entire assembly consisting of the piston, the threaded spindle and the motor can be displaced manually within the casing. Such a utilization is available when the casing in accordance with the invention is provided with a lateral cut-out through which the wax cartridge can be inserted. In this manner, the opportunity is available once the wax cartridge has been consumed for the piston to be displayed by manual intervention via the said cut-out back into its rearward position, i.e. the position which is suitable for inserting a new wax cartridge.

In the longitudinally-divided spindle nut, the two half-shells are accommodated in a bearing ring of elastomer material inside the stylus of the modeling device and moreover there are provided in a diametrically opposed position separating bodies which preferably comprise a wedge shape and which can be pressed in radially with respect to the likewise longitudinally-divided bearing ring in the gap between the two annular half-shells of the bearing ring, so that according to this movement a force can be exerted on the half-shells of the spindle nut, which force separates the said half-shells perpendicularly to their joint face. As a result of being received in the elastomer bearing ring, such a movement is likewise possible as the bearing ring deforms in an elastic manner and for this purpose it is designed accordingly in its dimensions and material. At the same time, in this manner the bearing ring serves to provide the necessary restoring force or it at least provides a contribution thereto. Moreover, it is advantageous to the invention that for the purpose of actuating the separating bodies an already existing sliding sleeve is involved. For example, the separating bodies can protrude slightly out of the outer surface of the modeling device, so that as a result of their "extending" on the outside they can be pressed inwards radially by means of the sliding sleeve. Likewise in the embodiment of this principle it can be provided that the wedge surfaces of the two separating bodies are connected to the bearing ring, for example adhered or vulcanized thereto and that as a result of extending over the radial outer sections of the separating wedges the material is displaced in a radially inwards direction and the bearing ring halves are removed from each other. When the bearing rings are in a state separated from each other in which the threaded engagement between the threaded spindle and the spindle nut is released, the separating bodies are thus elastically deformed, so that in turn restoring forces can be derived from this deformation state, which forces are released once the sliding sleeve has been removed and the bearing rings draw together, so that in turn a threaded engagement is produced between the spindle nut and the threaded spindle.

When the half-shells of the spindle nut are lying adjacent to each other their position is fixed in a from-locking manner relative to each other. This can be effected, for example, by means of engaging arrangements which are formed according to a type of tongue and groove connections, wherein a guiding effect can be exerted simultaneously on the half-shells by means of a conical design of the tongue and groove connections.

The drive principle mentioned in the first instance, where the spindle nut is only formed by one half-shell can be achieved in that the half-shell forms the closure of the cut-out in the wall of the casing of the modeling device, which cut-out is otherwise used to insert a wax cartridge. This means that the innerside of the half-shell is integrally provided with a threaded profile which extends over the peripheral angle of preferably 180°. This also means that the threaded engagement between this spindle nut and the threaded spindle can be released in an extraordinarily convenient manner, in that the said cut-out is merely revealed by removing the half-shell.

The modeling device is provided with a display device by means of which the user of the device is made aware of the extent to which the wax cartridge inserted has already been consumed, so that it might now be necessary imminently to insert a new wax cartridge. This is achieved by virtue of the fact that the displaced position of the piston, of the motor or any other function element which is connected to this assembly which can be displaced in the longitudinal direction of the device is visibly displayed towards the outside of the device. By way of example only, this can be achieved by means of a signal body which is integrally formed on the motor casing, wherein this signal body is accommodated in a sliding manner in an outer cut-out of the casing.

A spring provides the opportunity of holding the wax cartridge constantly in a defined position relative to the piston within the casing of the device. Thus, the wax cartridge can be fed forward at any time in a manner free of play. This condition has a favorable effect with respect to metering in a precise manner the wax which is to be dispensed. As a result of the wax cartridge being in a defined position within the casing, reproducible heating conditions can be created to the same extent, a condition which is of importance for the rapid readiness for service of the modeling device.

Owing to the fact that it is not possible to exclude reliably impurities from the substance in the wax cartridge but also owing to the extraordinarily small dimension of the through-flow cross-section of the modeling tip, it is always to be expected that these cross-sections will become blocked. However, owing to these small dimensions cleaning to free this cross-section of blockages is time-consuming. To avoid these problems a sieve or filter is provided which has a mesh or pore width which is designed with respect to retaining offending foreign bodies. This sieve is provided within the stylus in such a manner that it can be replaced, a characteristic which can be advantageously achieved by means of an insertion piece which is releasably connected to the innerside structures of the device. This connection can be by way of a screw connection, a bayonet closure or the like. The sieve is thus changed merely by handling the substantially larger insertion piece.

The quantity of liquid substance issuing from the modeling tip should be tailored as precisely as possible to suit the actual requirements with respect to working accuracy. However, owing to the liquid wax portions located within the modeling tip and within the part chambers adjacent thereto within the casing of the modeling device, switching off the forward feed is associated with an unavoidable after-flow of wax and in fact in dependence on the consistency of the temperature of the wax and the pressure conditions prevailing in the said part chambers. In order to prevent this problem, a switching valve is provided, which switching valve is located in an expedient manner at the outlet of the casing and in fact immediately up stream of the entry cross-section of the modeling tip. In preference, an electromagnetic switching valve is used for this purpose, which valve is controlled by the user by means of a sensor which is attached to the front side, i.e. to the side facing the modeling tip. When this valve is closed, any further liquid wax portions are prevented from flowing out of the through-flow channel of the modeling tip owing to the vacuum created as a result of closing the valve and owing to the capillary effect also exerted owing to the small cross-section dimensions. It is possible to trigger a closure of this valve automatically and this closure can be associated, as far as switching is concerned, with a termination of the forward feed.

A consequence of switching off the forward feed movement is initially characterized by the pressure conditions being maintained within the device, which results—as mentioned above—in a tendency for further substance to flow out of the modeling tip. This tendency is at least greatly reduced by virtue of the fact that the energy supply unit which also serves to control the forward feed is designed with the stipulation that once the forward feed procedure is completed, the piston is drawn back by a defined linear element, i.e. in the direction away from the modeling tip. This feature thus serves the comfort factor during the practical handling of the device and can likewise be automatically triggered according to predetermined linear elements. The linear elements are to be selected such that the spring mentioned in the introduction maintains its influence regardless of the piston having been drawn back.

Preferably the energy supply comprises an electric battery or can comprise an accumulator. The device in accordance with the invention can thus be operated independently from the mains.

The modeling tip is connected to the modeling device in such a manner that it can be replaced, so that if necessary in dependence upon the modeling procedures to be performed different modeling tips can be used. A triangular cross-sectional design of the elongated modeling device which in principle is similar to a writing device or stylus serves to improve the handling comfort.

The main area of application of the modeling device is the working procedure of applying wax in prosthodontics. The above described design principle can, however, be used in numerous other applications, where masses which are solid in their initial state, for example synthetic material, are applied in metered quantities to workpieces and must be modeled in a still flowing state. Finally one possible fundamental application is also during soldering procedures.

BRIEF DESCRIPTION OF THE DRAWINGS

FIG. 4 shows a partial illustration of an axial cross-section of the end facing the tip of the modeling device;

FIG. 5 shows an illustration similar to that shown in FIG. 4 of another embodiment of the modeling device;

FIG. 6 shows a partial illustration of an axial cross-section of the end of a modeling device remote from the tip;

FIG. 7 shows a partial illustration of a lateral view of a detail VII of FIG. 6;

FIG. 8 shows an end view of the component illustrated in FIG. 7 according to the line of view VIII;

DETAILED DESCRIPTION OF EMBODIMENTS

Figure 1:
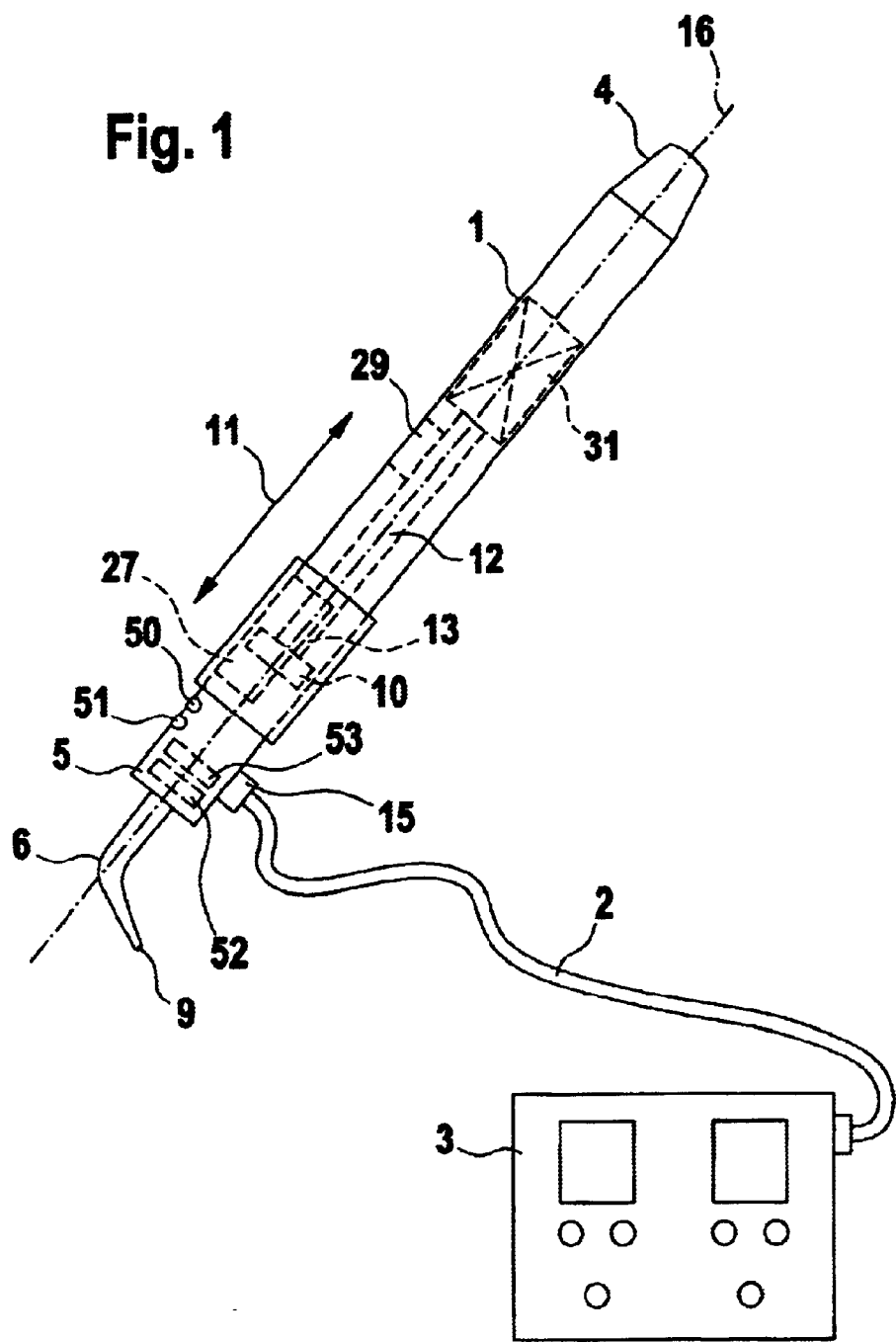
FIG. 1 shows a view of the modeling device in accordance with the invention.
Figure 2:
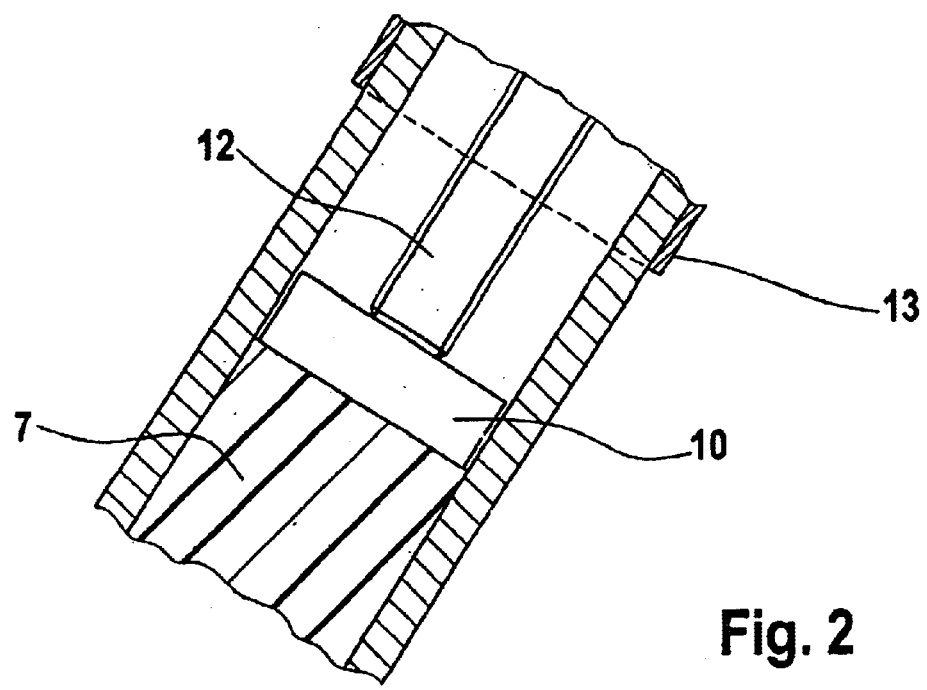
FIG. 2 shows an enlarged partial illustration of an axial cross-section of a region II of the modeling device in accordance with the invention.
Figure 3:
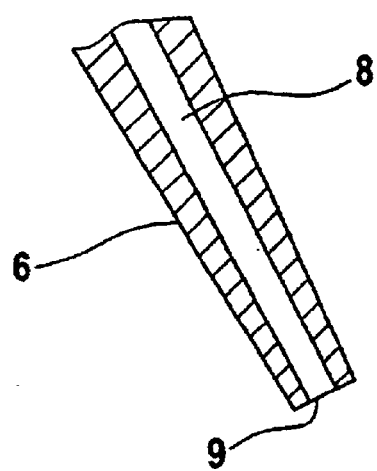
FIG. 3 shows an enlarged partial illustration of an axial cross-section of the tip of the modeling device in accordance with the invention.

The modeling device in accordance with the invention illustrated in FIGS. 1 to 3 consists generally of a modeling device 1 which is to be guided manually and which is connected via a cable 2 to an energy supply unit 3. The energy supply unit 3 is designed for connection to a conventional electric mains and for providing an output voltage and an output current which are dimensioned and can in particular be regulated in dependence upon the electrical functions of the modeling deice 1. The energy supply unit can thus generally also be designed for control purposes.

The modeling device 1 consists of a tubular base body or stylus, whose region facing an end 4 is intended and designed inter alia for the purpose of receiving a forward feed drive and whose end 5 lying opposite thereto is intended and designed for the purpose of receiving in an interchangeable manner a modeling or substance dispensing tip 6.

The part of the base body facing the modeling tip 6 is designed as a hollow chamber which is intended to receive a rod-shaped wax body 7. It is essential that the part of the hollow chamber facing the end 5 and in particular the modeling tip 6 are capable of being heated electrically and this is achieved by virtue of the fact that these parts are disposed in an electrically insulated manner with respect to the other sections of the base body and are designed as parts of an electric conductor in the form of heating coils 52 and 53 which can thus be heated according to the voltage influence. The said hollow chamber is also connected to allow through-flow to the central channel 8 of the modeling tip 6, whose outlet is open.

The said wax cartridge 7 is moreover dimensioned such that the cross-section of the hollow chamber is filled and this wax cartridge 7 lies on its end remote from the modeling tip 6 on a piston 10 which is received in a slidable manner within the base body of the modeling device 1 in the direction of the arrow 11.

The numeral 12 designates a threaded spindle, one end of which is connected to the piston 10, which is received in a non-rotatable manner within the base body, and the other end of which is received in a non-rotatable, fixed spindle nut 29, shown in detail in FIG. 6. The threaded spindle 12 can rotate by means of an electromotor 31 which is disposed within the base body as shown in FIGS. 1 and 6. A rotation of the spindle is thus converted accordingly into an axial movement of the piston 10 (along with motor 31) in the direction of the arrow 11 by the engagement of the threaded spindle 12 with the spindle nut 29.

The said body is provided on its region facing the end 5 with a cut-out or opening 27, which is approximately the length of a sliding sleeve 13 which can be displaced along the base body for the purpose of reve aling or closing this cut-out. This cut-out 27 is dimensioned such that a wax cartridge 7 can be inserted into the said hollow chamber of the base body.

The modeling tip 6 consists of a first part which extends in the axial direction of the base body and a part which is bent at an angle with respect thereto in an inclined manner in relation to the axis thereof and terminates in the outlet 9.

Two sensor switches 50 and 51, shown in FIG. 1, serve on the one hand to control the motor 31 allocated to the piston 10 (switch 50) and on the other hand to control the heating energy which is to be transmitted to the heating coils 52 and 53 for heating the end region of the wax cartridge and or the wax located within the channel 8 (switch 51). In a particularly advantageous manner, the channel 8 can comprise a cross-section which widens as it progresses in the direction towards the outlet 9.

Basic heating is provided, in particular regulated, regularly via the energy supply unit 3, so that only power peaks are controlled via the corresponding sensor switch on the modeling deice 1 for the heating requirements. These power peaks can preferably be utilized for heating the metallic modeling tip 6.

Figure 11:
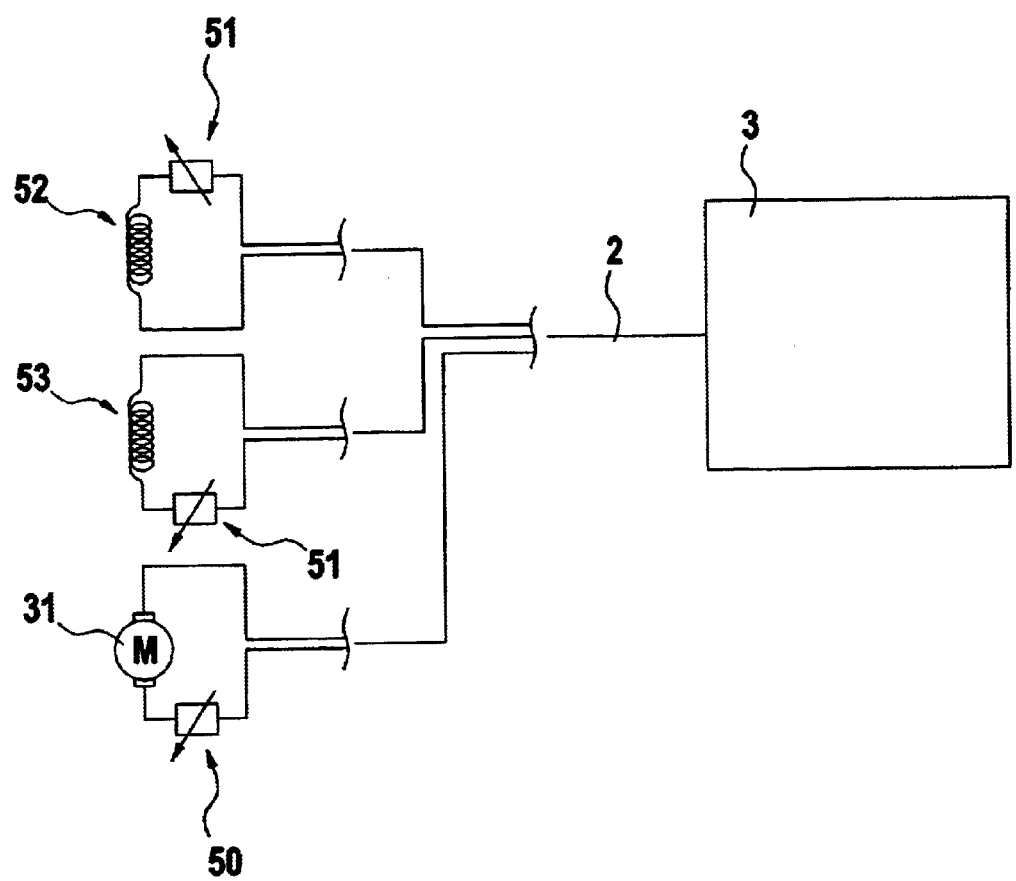
FIG. 11 is a schematic electrical diagram.

FIG. 11 provides a schematic electronic diagram illustrating the circuits of the modeling device whereby electrical power from supply 3 is delivered to the device via cable 2. Power to the electrical motor 31 is controlled by means of switch 50, and power to heating coils 52 and 53 being controlled by switch 51, both switches 50 and 51 being mounted on the device.

The cable 2 is attached in accordance with the invention to the front side end 5 of the base body, i.e. the end 5 of the base body facing the modeling tip. In reality, the connection point of the cable 2 can be disposed approximately in the region of the front third of the longitudinal extension of the base body. For this purpose, the base body is provided with a connection point 15 by means of which the cable 2 is routed out of the base body at a right angle with respect to the longitudinal axis 16. It is also possible to have an obtuse angle, so that the cable 2 is routed towards the rearward end of the base body, i.e. the end remote from the modeling tip.

In a particularly advantageous manner, the connection point 15 can be provided directly on the front-side end of the base body. In this case, the application and the function of a sliding sleeve 13 (FIG. 1) is not impaired.

As illustrated in FIG. 1, the modeling tip is formed curved with respect to the longitudinal axis 16 of the modeling device 1 and extends at an obtuse angle with respect to this longitudinal axis. For reasons relating to the operating technology, the connection point 15 for the cable 2 is located on the concave curved side of the modeling tip 6, so that when working with the device the cable exits towards the lower side and does not impair the handling opportunities of the device.

In place of a sliding sleeve 13 it is possible in this case, insofar as the spacial positioning of the connection point 15 makes this necessary, to provide another flap or sliding element by means of which a cut-out in the base body can be revealed or closed, which serves for the insertion of wax cartridges into the modeling device 1.

The main application area of the modeling device 1 in accordance with the invention is the application of wax for example to the curve region of the tooth base body of a prosthesis and for this purpose a wax body 7 is inserted into the modeling device 1. Then, electrical energy is supplied to the modeling device 1 by means of the energy supply unit 3 via the cable 2 in a quantity such that on the one hand by actuating the respective sensor switch the said motor can be activated and as a consequence the wax body 7 is displaced in the direction towards the end 5 of the base body. Likewise by actuating another sensor button the end region of the wax substance can be electrically heated, so that depending upon the supply movement generated via the piston 10 liquid wax exits from the outlet 9 of the modeling tip 6 and by means thereof is applied to the tooth base body where it is subsequently modeled. It is essential in this connection, that the motor is designed in connection with the said threaded spindle 12 with regard to its electrical parameters such that it is possible to regulate preferably in a continuous manner the rotational speed and thus the forward feed within a control range.

The control unit allocated to the motor can be designed in an advantageous manner such that the piston 10 is automatically moved to its rearward position, i.e. the position lying at the end of the base body remote from the modeling tip 6, as soon as an obstacle, jamming or the like occurs during the forward feed of the wax body 7. This problematic state can be signaled optically and acoustically.

Moreover, the electrical concept of the heating arrangement can be designed in such a manner that even without actuating the sensor, pre-heating occurs, however, this does not lead to wax issuing out of the outlet 9. On the other hand, as a consequence of actuating the sensor more comprehensive heating can be achieved, particularly in the region of the modeling tip, and thus liquid wax issues out of the said outlet. Moreover, the heating of the wax substance controlled in this way by means of a sensor can be designed advantageously such that the quantity of heat being introduced can be controlled within a control range, so that in the region of the outlet 9 wax is available in a quantity and in a consistency necessary for the modeling procedure. The energy supply unit 3 can be used to regulate a basic heat requirement.

Irrespective of the connection site of the cable 2 to the base body of the modeling device 2, grooves can be provided on the innerside of the base body for the purpose of receiving electric lines, by means of which on the one hand the said motor and on the other hand the heating device located on the end 5 of the base body can be supplied with electrical energy.

However, the cable 2 attached to the connection point 15 can also extend at an optional angle with respect to the longitudinal axis of the modeling device 1 or can be attached thereto.

Referring to FIGS. 4 to 10, further exemplified embodiments of the modeling device in accordance with the invention will be described herein under and again function elements which correspond to those of FIGS. 1 to 3 will be designated with like numerals, so that it will not be necessary to repeat a description thereof.

An essential feature of the exemplified embodiment illustrated in FIG. 4 of a modeling device 18 is an insertion piece 19 which is screwed into a corresponding threaded bore of the casing of the modeling device 18 by way of a front-side threaded section 20 which is disposed facing the end 5. The threaded section 20 comprises a smaller diameter than the adjacent thereto, remaining base body of the insertion piece 10 and encompasses a cylindrical hollow space 21 which extends coaxially with respect to the longitudinal axis 16 of the modeling device 18. Bores 22,23 likewise extend in a coaxial manner with respect to this longitudinal axis 16 and by means of these said bores the hollow chamber 21 [is connected] on the one hand to the chamber intended for receiving the wax body 7 and on the other hand to the channel 8 of the modeling tip 6. The insertion piece 19 encompasses on its end remote from the threaded section 20 for its part a hollow chamber 24 which generally extends in a conical manner in the direction towards the wax cartridge 7.

A fine mesh sieve 25 is disposed within the hollow chamber 21 and must be attached in such a manner that the liquid wax flowing through this hollow chamber 21 cannot cause the position of the said sieve to change.

The likewise-mentioned further hollow chamber 24 of the insertion piece 19 serves to receive a spring 26, one end of which rests against the facing surface sections of the hollow chamber 24 and the opposite end of which rests against the facing end side of the wax body 7.

The spring 26 acts in such a manner that the wax body 7 is in constant contact with the piston 10 (FIG. 2) and thus has a defined starting position. In order to avoid an excessive quantity of heat being transmitted to the wax body 7 by way of the generally metal spring, it is possible to dispose at the point of contact between the spring 26 and the wax body 7 an insulating element [not illustrated in the drawing] which consists of a material which has a lower caloric conductibility Illustrated in the drawing in FIG. 4 is a cut-out or opening 27 which can be revealed or closed by means of displacing the sliding sleeve 13 in the direction of the arrow 11, for example, for the purpose of inserting a new wax body 7 into the modeling device 18 once a wax body has been consumed.

The exemplified embodiment illustrated in FIG. 5 of a modeling device differs from the one shown in FIG. 5 merely by the fact that a sieve 25 is now received within the hollow chamber 24 of the insertion piece 19.

The arrangement of a sieve 25 on the output side with respect to the modeling device increases the operating reliability as the finest impurities in the substance of the wax body are practically unavoidable and these impurities can create problems, particularly in the region of the channel 8 of the modeling tip 6, which regularly prevent the throughflow of the liquid wax. The work involved in cleaning the modeling tip 6 is relatively troublesome and time-consuming owing to the extremely small diameter of the tip, so that the arrangement of a sieve can remedy this.

Figure 9:
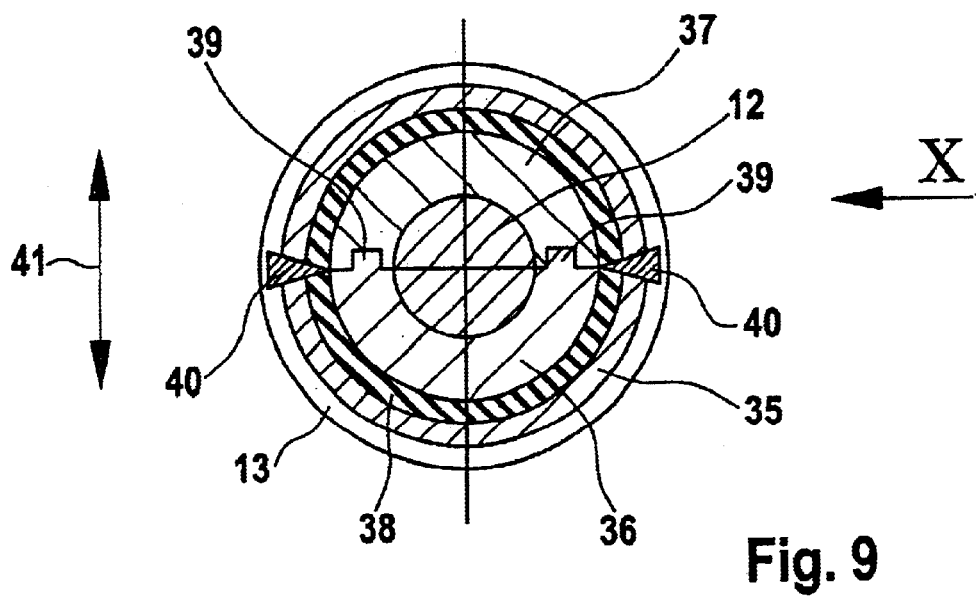
FIG. 9 shows a cross-sectional illustration of a further embodiment of a device in accordance with the invention according to the cutting plane IX—IX of FIG. 10.

FIGS. 7 to 9 illustrate an exemplified embodiment of the drive concept of a modeling device 28 in accordance with the invention. The numeral 29 designates the spindle nut in the form of a half-shell which is inserted into a corresponding cut-out of the casing of the modeling device 28 and is latched preferably in an elastic manner in the inserted position. A magnetic securing arrangement is also possible. However, relevant latching means are not illustrated in the drawing. The half-shell 29 closes the cut-out which is intended for the insertion of the wax bodies and the half-shell 29 in the inserted state forms a component of the casing wall of the modeling device 28, which is encompassed by the sliding sleeve 13.

The half-shell 29 is provided at one of its ends in one piece with a threaded section 30 which is intended for engagement with the thread of the threaded spindle 12. The half-shell 29 is thus held in the installed state in a non-rotatable manner relative to the longitudinal axis 16 of the modeling device 28. The threaded section 30 extends starting from the one end of the half-shell 29 over only a partial length thereof, whereas the half-shell also follows on the innerside the peripheral region of the casing of the modeling device 28 and is thus designed for the purpose of guiding the piston 10. It is essential that the piston 10 is guided, within the chamber formed in this way, likewise in a non-rotatable manner with respect to the longitudinal axis 16.

In the illustration as shown in FIG. 6, the half-shell 29 is secured in a form-locking manner as a result of the sliding sleeve 13 being pushed over in its assembly position. This is only to be understood as an example. Thus, a possible security component is a sleeve which can rotate on the base body around the axis thereof and which is provided with a cut-out for the purpose of removing the half-shell, so that depending upon the rotational angle position of this sleeve, the half-shell is again secured in a form-locking manner.

The threaded spindle 12 is drivingly connected at its end remote from the piston 10 to a motor 31, in this case an electromotor which is likewise guided within the casing of the modeling device 28 in such a manner as to be non-rotatable about the longitudinal axis 16. It is evident that in the case of this constellation depending upon the direction of rotation transmitted via the motor 31 to the threaded spindle 12 the entire assembly, consisting of the motor 31, the threaded spindle 12 and the piston 10, can be moved in a straight line in the direction of the arrow 11.

The drawing in FIG. 6 illustrates the piston 10 in its one boundary position, in which after the sliding sleeve 13 has been displaced accordingly and the half-shell 29 removed a new wax body can be inserted into the modeling device. In this connection, the illustrated device still offers the advantage that after dismantling the half-shell 29 the piston 10 can be displaced in the most convenient manner manually into its rearward boundary position illustrated in FIG. 6.

Moreover, the illustrated function principle can be modified in many ways. Accordingly, a further half-shell-like threaded section can lie opposite the half-shell 29, in particular its threaded section 30, which half-shell-like threaded section is disposed likewise in a non-rotatable manner relative to the longitudinal axis 16, so that the threaded spindle 12 is guided through a complete non-rotatably disposed threaded profile. However, in this case the advantage of the convenient manual sliding back of the piston 10 no longer exists after a wax body has been consumed.

In addition, whilst maintaining the drive concept, a threaded profile 30 can be disposed moreover also in an axially fixed and non-rotatable manner at a different site of the inner chamber of the casing of the modeling device 28.

The numeral 32 designates an elongated orifice in the wall of the modeling device 28 which is closed on the outer side by means of a transparent cover 33. The cover 33 terminates flush with the outer surface of the modeling device 28 and comprises a thickness which is substantially less than the thickness of the wall of the device casing. A, for example, cuboid-shaped signal body 34 is accommodated within the remaining thickness region of the orifice 32 and this signal body is in fixed connection with the motor 31. The signal body 34 comprises in an expedient manner a particular coloring so that its position can be easily recognized along the orifice 32.

The orifice 32 is preferably designed according to such a longitudinal extension which corresponds in general to the displacement feature of the motor 31, so that it is possible using the position of the signal body 34 to recognize the extent to which the wax body inserted in the modeling device has already been consumed. If necessary, it is also possible in this case to provide a scale on the outer side of the device, which displays the residual content of wax which is capable of being processed.

Figure 10:
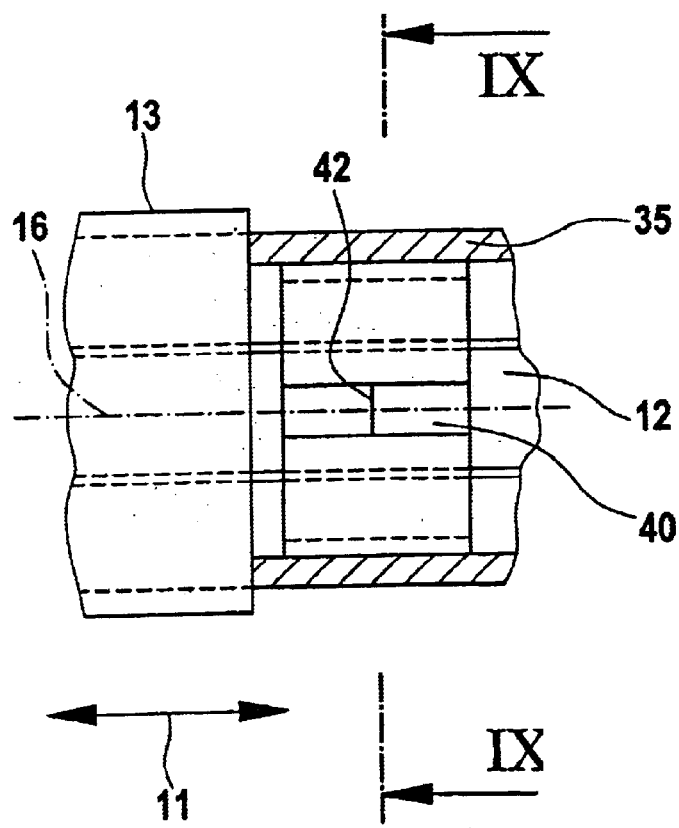
FIG. 10 shows a lateral view in a partial cross-sectional illustration of the device in accordance with the invention illustrated in FIG. 9.

FIGS. 9 and 10 illustrate a further possible embodiment of the drive concept of the invention. The threaded spindle 12 in this case engages with a longitudinally-divided spindle nut which thus consists of two half-shells 36, 37 and is disposed, whilst providing an intermediate arrangement of a bearing ring 38 which consists of an elastic material, for example an elastomeric material, in the modeling device 35 axially in a non-displaceable manner and with respect to the longitudinal axis 16 in a non-rotatable manner. For example, the bearing ring 38 can consist of rubber which is adhered on the one side to the facing surfaces of the modeling device 35 and on the other side to the half-shells 36, 37. For the purpose of ensuring a clear assembly position of the two half-shells 36, 37, the said half-shells engage in their joint face in a form-locking manner. For this purpose, two strip-like projections 39 are formed as one on the half shell 36 and in fact protruding out of the joint face and these projections are inserted in corresponding opposite grooves of the half-shell 37 and the position of the two half-shells is stabilized relative to each other.

The bearing ring 38 is divided longitudinally and separating bodies 40, which are wedge-shaped in a mutually diametrically opposite manner and are dimensioned and created in the same manner with respect to each other, protrude into the gap, which extends in the direction of the longitudinal axis 16, between the two half-shells of the bearing ring 38. Moreover, these separating bodies penetrate cut-outs in the casing of the modeling device which extend in the longitudinal direction of the modeling device 35 and can in addition, as illustrated in FIG. 10, comprise in the longitudinal direction 16 on both sides with respect to a middle plane a ramp-like downward inclining section, i.e. section which protrudes on the outer surface of the casing wall of the modeling device 35. In addition, the separating bodies 40 are designed with the stipulation that as a result of the sliding sleeve 13 being pushed over they are displaced radially inwards with respect to the modeling device 35 and as a result of their wedge-shaped design they exert separating forces in the direction of the arrows 41 onto the two half-shells 36, 37. Furthermore, the separating bodies 40 are dimensioned and designed to such an extent that by way of these separating forces, the half-shells 36, 37 under elastic compression of the half-shells, which cooperate therewith, of the bearing ring 38 are removed so far away from each other that a threaded engagement between the inner thread of the half-shells 36, 37 and the threaded spindle 12 is released. This state is achieved if the sliding sleeve 13 has reached the summit point 42 of the separating bodies 40, so that as a consequence of the piston 10 (FIG. 2) and therewith the entire assembly consisting of the threaded spindle 12 and the motor attached thereto can be manually displaced back into its rearward position.

Further numerous modifications of the subject of the application are possible. Accordingly an energy supply unit 3 which cooperates with the motor 31 can be designed to the extent that after the motor has completed the forward feed, i.e. after a force is exerted on the wax body 7 which displaces said wax body in the direction towards the end 5, automatically a rearward movement of the piston 10 away from the end 5 by a selectable path element is initiated. This feature can contribute to preventing further liquid wax from flowing out of the modeling tip 6.

Moreover, the modeling device can be provided on its end 5 with a preferably electromagnetically actuated valve, by means of which the flow of wax into the modeling tip can be released or blocked. Also in this manner, further wax can be prevented from flowing, wherein it is assumed that in the case of the extremely small cross-sectional dimensions of the channel 8 within the modeling tip 6 the wax present in this channel is also held back as a result of the capillary effect exerted thereon.

Thus, numerous measures are undertaken which render it possible to work with the modeling device in an extremely comfortable manner and to meter in an extremely precise manner the quantity of liquid wax which issues out of the outlet of the modeling tip 6.

What is claimed is:

1. A modeling device for manually applying a modeling substance that flows when heated, said device comprising:
   an elongated stylus having first and second ends oppositely disposed, a chamber positioned within said stylus and extending lengthwise there along;
   a substance dispensing tip projecting from said first end, said tip having a bore in fluid communication with said chamber;
   a closable opening in said stylus adjacent to said first end for positioning said modeling substance in solid form within said chamber;
   a heating element positioned at said first end for heating said modeling substance at said first end to liquid form for flowing from said chamber through said bore and out from said tip;
   a piston movably mounted within said chamber between said first and said second ends, said piston being engageable with said modeling substance for forcing said substance toward said first end;
   a threaded spindle attached to said piston and extending therefrom toward said second end of said stylus;
   a spindle nut positioned within said chamber between said piston and said second end of said stylus;
   an electric motor movably positioned within said chamber between said spindle nut and said second end of said stylus, said motor engaging said spindle for moving said piston;
   a motor control switch mounted on said stylus for manually controlling said motor;
   a heating control switch mounted on said stylus for manually controlling said heating element;
   an energy supply and control unit; and
   an electrical cable extending from said energy supply and control unit and attached to said stylus at said first end.

2. A modeling device according to claim 1, wherein said heating element comprises an electrical resistance coil for heating said modeling substance and converting it into a flowable state.

3. A modeling device according to claim 2, wherein said heating element further comprises a plurality of electrical resistance coils, each of said coils being separately controllable and having different heating capacities from one another for heating said modeling substance and converting it into a flowable state.

4. A modeling device according to claim 3, wherein said heating element is controllable in relation to the characteristics of the modeling substance for heating said modeling substance and converting it into a flowable state.

5. A modeling device according to claim 3, wherein said substance dispensing tip is heated by said heating element in a controllable manner.

6. A modeling device according to claim 2, wherein said motor control switch comprises a first sensor switch and said heating control switch comprises a second sensor switch, said first sensor switch for controlling said motor for motion of said piston thereby regulating flow of said modeling substance, said second sensor switch for controlling said heat energy to said heating element for heating said modeling substance.

7. A modeling device according to claim 1, wherein said substance dispensing tip comprises an end section that is angularly oriented with respect to said stylus.

8. A modeling device according to claim 7, wherein said motor control switch comprises a first sensor switch and said heating control switch comprises a second sensor switch, said first sensor switch for controlling said motor for motion of said piston thereby regulating flow of said modeling substance, said second sensor switch for controlling said heat energy to said heating element for heating said modeling substance.

9. A modeling device according to claim 7, wherein said dispensing tip is removably attached to said stylus.

10. A modeling device according to claim 1, wherein said motor control switch comprises a first sensor switch and said heating control switch comprises a second sensor switch, said first sensor switch for controlling said motor for motion of said piston thereby regulating flow of said modeling substance, said second sensor switch for controlling said heat energy to said heating element for heating said modeling substance.

11. A modeling device according to claim 10, wherein said electric motor is controllable for controlling motion of said piston in relation to the characteristics of the modeling substance for feeding said modeling substance to said dispensing tip.

12. A modeling device according to claim 10, wherein said substance dispensing tip is heated by said heating element in a controllable manner.

13. A modeling device according to claim 10, further comprising an end switch which controls said motor and causes said piston to move from said first end toward said second end.

14. A modeling device according to claim 10, further comprising a display device positioned within said chamber, said display device for indicating the motion of one of said piston and said motor within said chamber.

15. A modeling device according to claim 14, further comprising:
    an orifice positioned in said stylus;
    a signal body being integrally formed with said motor, motion of said signal body being guided within said orifice.

16. A modeling device according to claim 10, further comprising a valve positioned within said chamber proximate to said dispensing tip for controlling flow of said modeling substance.

17. A modeling device according to claim 16, further comprising a selectable path element adapted to move said piston in a direction away from said dispensing tip upon completion of movement of said piston toward said dispensing tip.

18. A modeling device according to claim 17, wherein said energy supply and control unit comprises an electric battery.

19. A modeling device according to claim 16, wherein said energy supply and control unit comprises an electric battery.

20. A modeling device according to claim 1, wherein said heating element is controllable in relation to the characteristics of said modeling substance for heating said modeling substance and converting it into a flowable state.

21. A modeling device according to claim 1, wherein said electric motor is controllable for controlling motion of said piston in relation to the characteristics of the modeling substance for feeding said modeling substance to said dispensing tip.

22. A modeling device according to claim 21, further comprising an end switch which controls said motor and causes said piston to move from said first end toward said second end.

23. A modeling device according to claim 21, further comprising a valve positioned within said chamber proximate to said dispensing tip for controlling flow of said modeling substance.

24. A modeling device according to claim 1, wherein said substance dispensing tip is heated by said heating element in a controllable manner.

25. A modeling device according to claim 21, further comprising a display device positioned within said chamber, said display device for indicating the motion of one of said piston and said motor within said chamber.

26. A modeling device according to claim 1, further comprising an end switch which controls said motor and causes said piston to move from said first end toward said second end.

27. A modeling device according to claim 26, wherein said spindle nut is positioned within said stylus in a non-displaceable and non-rotatable manner, said motor being held in a displaceable but non-rotatable manner within said stylus.

28. A modeling device according to claim 1, wherein said spindle nut is positioned within said stylus in a non-displaceable and non-rotatable manner, said motor being held in a displaceable but non-rotatable manner within said stylus.

29. A modeling device according to claim 28, wherein said spindle nut comprises a half shell that is releasably connected to said stylus.

30. A modeling device according to claim 29, wherein said half shell is adapted to close said opening in said stylus, said half shell having an inwardly facing threaded section that cooperates with said threaded spindle.

31. A modeling device according to claim 28, wherein said spindle nut comprises two half shells engageable with one another to form a full cylindrical shell surrounding said threaded spindle, said half shells being movable relative to one another within said stylus between a first position engaging said threaded spindle, and a second position released from engagement with said threaded spindle.

32. A modeling device according to claim 31, further comprising:
   each half shell having a joint face providing an interface for engagement of said half shells with one another to form said full shell;
   a plurality of separating bodies being insertable between said half shells to exert a force on each half shell perpendicular to said joint faces for effecting movement of said half shells between said first and second positions; and
   a sleeve slidably movable over said half shells and engageable with said separating bodies for effecting exertion of said force on said half shells for separation thereof at said joint face.

33. A modeling device according to claim 32, wherein said half shells are secured in a form-locking manner at least at said joint faces and in a direction perpendicular to the length of said stylus.

34. A modeling device according to claim 31, further comprising a bearing ring positioned within said chamber and formed of an elastomeric material, said half shells being mounted within said bearing ring.

35. A modeling device according to claim 31, wherein each half shell has a joint face providing an interface for engagement of said half shells with one another, said half shells being secured in a form-locking manner at least at said joint faces and in a direction perpendicular to the length of said stylus.

36. A modeling device according to claim 31, further comprising:
   each half shell having a joint face providing an interface for engagement of said half shells with one another, said half shells being secured in a form-locking manner at least at said joint faces and in a direction perpendicular to the length of said stylus.

37. A modeling device according to claim 1, further comprising a display device positioned within said chamber, said display device for indicating the motion of one of said piston and said motor within said chamber.

38. A modeling device according to claim 1, further comprising a spring positioned within said chamber at said first end, said modeling substance in solid form being positionable within said chamber and having an end engageable with said spring.

39. A modeling device according to claim 1, further comprising a sieve positioned between said chamber and said substance dispensing tip.

40. A modeling device according to claim 39, further comprising a sieve positioned between said chamber and said substance dispensing tip.

41. A modeling device according to claim 40, further comprising a carrier positionable within said first end of said stylus by means including screw threads, said carrier adapted for mounting said sieve within said chamber.

42. A modeling device according to claim 40, wherein said dispensing tip is removably attached to said stylus.

43. A modeling device according to claim 39, wherein said dispensing tip is removably attached to said stylus.

44. A modeling device according to claim 1, further comprising a valve positioned within said chamber proximate to said dispensing tip for controlling flow of said modeling substance.

45. A modeling device according to claim 44, further comprising a valve positioned within said chamber proximate to said dispensing tip for controlling flow of said modeling substance.

46. A modeling device according to claim 44, wherein said dispensing tip is removably attached to said stylus.

47. A modeling device according to claim 1, further comprising a selectable path element adapted to move said piston in a direction away from said dispensing tip upon completion of movement of said piston toward said dispensing tip.

48. A modeling device according to claim 1, wherein said energy supply and control unit comprises an electric battery.

49. A modeling device according to claim 1, wherein said dispensing tip is removably attached to said stylus.

50. A modeling device according to claim 1, wherein said stylus has a triangular cross section.

* * * * *

UNITED STATES PATENT AND TRADEMARK OFFICE
CERTIFICATE OF CORRECTION

PATENT NO. : 6,794,612 B2  Page 1 of 1
DATED : September 21, 2004
INVENTOR(S) : Furtwangler It is certified that error appears in the above-identified patent and that said Letters Patent is hereby corrected as shown below:

Title page,
Item [30], Foreign Application Priority Data, "Apr. 5, 2000" should read -- May 4, 2000 --

Column 15,
Line 21, change "21" to -- 24 --

Signed and Sealed this

Fifteenth Day of February, 2005

JON W. DUDAS
*Director of the United States Patent and Trademark Office*